United States Patent
Bechwati et al.

(10) Patent No.: US 6,687,326 B1
(45) Date of Patent: Feb. 3, 2004

(54) METHOD OF AND SYSTEM FOR CORRECTING SCATTER IN A COMPUTED TOMOGRAPHY SCANNER

(75) Inventors: Ibrahim M. Bechwati, Roslindale, MA (US); Carl R. Crawford, Brookline, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 10/121,466

(22) Filed: Apr. 11, 2002

Related U.S. Application Data

(60) Provisional application No. 60/283,075, filed on Apr. 11, 2001.

(51) Int. Cl.$^7$ ............................................. G01N 23/203
(52) U.S. Cl. ................................................ 378/7; 378/70
(58) Field of Search .............................. 378/4, 7, 20, 70, 378/86, 87, 88

(56) References Cited

U.S. PATENT DOCUMENTS

| | | | |
|---|---|---|---|
| 4,807,267 A | * | 2/1989 | Rifu et al. ....................... 378/7 |
| 5,602,895 A | * | 2/1997 | Fivez et al. .................. 378/98.4 |
| 5,615,279 A | * | 3/1997 | Yoshioka et al. ............ 382/131 |
| 5,905,809 A | | 5/1999 | Timmer ....................... 382/131 |
| 5,949,842 A | | 9/1999 | Schafer et al. .................. 378/4 |
| 5,970,113 A | | 10/1999 | Crawford et al. .............. 378/19 |
| 6,175,609 B1 | | 1/2001 | Edic et al. ....................... 378/7 |
| 6,256,367 B1 | | 7/2001 | Vartanian ........................ 378/7 |

OTHER PUBLICATIONS

G. H. Glover, "Compton Scatter Effects In CT Reconstructions", Med. Phys. 9(6), Nov./Dec. 1982, 1982 Am. Assoc. Phys. Med., pp. 860–867.

* cited by examiner

*Primary Examiner*—Drew A. Dunn
*Assistant Examiner*—Hoon K. Song
(74) *Attorney, Agent, or Firm*—McDermott, Will & Emery

(57) ABSTRACT

A system for correcting for scatter in a computed tomography scanner includes a tunnel having a platform disposed therein for receiving an object to be scanned, an x-ray source for directing x-rays at the object to be scanned, a detector array including a plurality of primary detectors for receiving the x-rays and at least one secondary detector for receiving portion of the x-ray beam scattered within the tunnel. The system further includes processing means for reducing the effects of scatter in images of the object reconstructed from the x-rays detected by method of estimating an amount of scatter caused only by the presence of the object corrected by an amount of scattered x-ray when presence or absence of object.

2 Claims, 9 Drawing Sheets

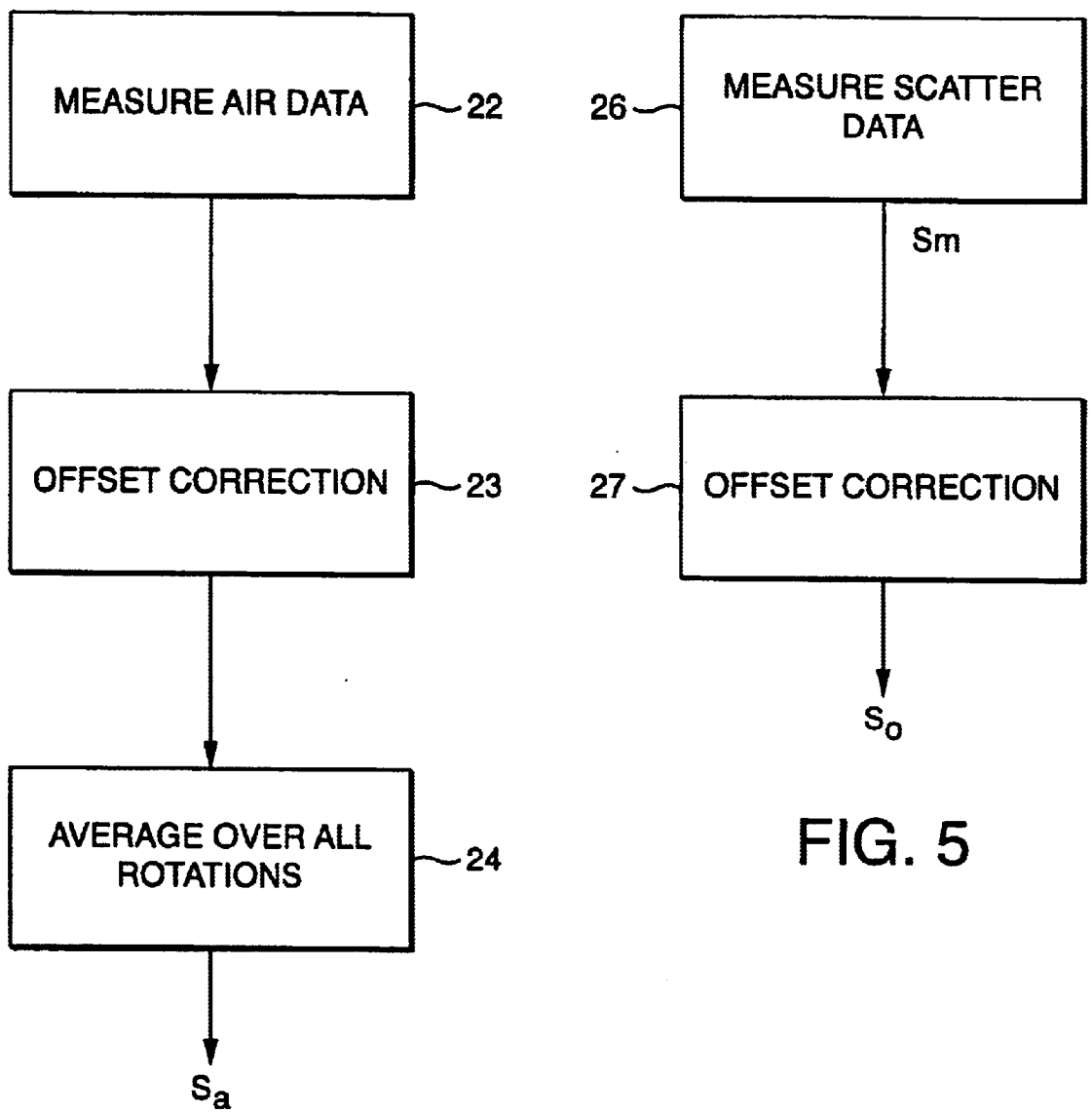

METHOD OF AND SYSTEM FOR CORRECTING SCATTER IN A COMPUTED TOMOGRAPHY SCANNER

RELATED APPLICATIONS

This application claims the benefit of U.S. Provisional Patent Application Serial No. 60/283,075, filed Apr. 11, 2001, entitled SCATTER CORRECTION FOR CT SCANNER, which application is hereby incorporated by reference in their entirety.

FIELD OF THE INVENTION

The present invention relates generally to a method of and system for correcting scatter in a computed tomography (CT) scanner, and more particularly to a method of and system for determining the x-ray scatter present in the scanner chamber prior to obtaining scans of the target object, in order to compensate for scatter caused by static elements in the scanner chamber.

BACKGROUND OF THE INVENTION

Elastic scattering results from the interaction of photons of an x-ray beam with atoms of a scanned object. The x-ray photons cause electrons of the scanned object to vibrate while still bound to their orbits around the nuclei. The electrons re-radiate the x-ray energy in all directions. The amount of scattering depends on the effective atomic number of the impinged atom, as it will increase for atoms having a higher atomic number. Since elastic scattering is a resonant phenomenon the electrons remain bound to the atoms, and the photons are not absorbed by the scanned object. Compton scattering, which is more significant, is due to the direct exchange of energy between the x-ray photon and an electron with which it collides. Part of the photon energy is absorbed by the electron and converted into kinetic energy. The photon is then scattered at a lower energy level. While most of the photons are attenuated within the scanned object, a small portion of photons are not absorbed, resulting in an increase in scatter radiation as part of the primary x-ray beam.

Scattering causes artifacts in images reconstructed from the x-rays. It adversely affects image contrast and generates streaks from high-density objects. The increase in counts due to scattering reduces the measured densities, resulting in reduced contrast of scanned objects in the reconstructed images. Scattering also causes cupping and blurring similar to the beam hardening artifact in large bulk objects.

An exact solution to the problems caused by scatter cannot be determined due to the randomness of the scattering process. Some prior art systems utilize anti-scatter plates which are disposed between the detectors of a detector array and which act to reduce the amount of scatter that reaches each detector, so that the detector receives mostly x-rays that travel to the detector in a direction substantially perpendicular to the detector. However, anti-scatter plates are extremely expensive and add structural complexity to the scanners. Another prior art approach to reducing scatter in an x-ray scanner is to estimate the amount of scatter in a scanner system using either constant scatter values or values that are obtained with Monte-Carlo simulations. These systems may or may not utilize anti-scatter plates. However, these systems are not able to account for scatter caused by the scanner tunnel and conveyor, which are within the field of view of the x-ray beam.

SUMMARY OF THE INVENTION

The present invention utilizes scatter detectors to measure the amount of scatter within the scanner before an object to be scanned is placed therein and scanned. This scatter data is used to determine the amount of scatter caused by the object being scanned, so that the scatter associated with the object can be compensated for.

According to a first embodiment of the invention, a system for correcting for scatter in a computed tomography scanner includes a tunnel having a platform disposed therein for receiving an object to be scanned, an x-ray source for directing x-rays at the object to be scanned, a detector array including a plurality of primary detectors for receiving the x-rays and at least one secondary detector for receiving portions of the x-ray beam scattered within the tunnel. The system further includes processing means for reducing the effects of scatter in images of the object reconstructed from the x-rays detected by the primary detectors, the processing means performing the steps of:

A. determining an amount of scatter detected by the at least one secondary detector resulting from the tunnel and the platform prior to the placement of the object on the platform;

B. determining an amount of scatter detected by the at least one secondary detector resulting from the tunnel, the platform and the object after the object has been placed on the platform;

C. estimating an amount of scatter caused only by the presence of the object on the platform within the tunnel; and D. correcting the reconstructed images of the object based on the amount of scatter estimated in Step C.

According to another embodiment of the present invention, a method of correcting for scatter in a computed tomography scanner having a platform for receiving an object to be scanned, the platform being disposed within a tunnel, a primary detector array for detecting x-rays provided by and x-ray source and a secondary detector array for detecting scattered x-rays from the x-ray source is disclosed. The method includes:

A. determining an amount of scatter detected by the secondary detector array resulting from the tunnel and the platform prior to the placement of the object on the platform;

B. determining an amount of scatter detected by the secondary detector array resulting from the tunnel, the platform and the object after the object has been placed on the platform;

C. estimating an amount of scatter caused only by the presence of the object on the platform within the tunnel; and D. correcting reconstructed images of the object based on the amount of scatter estimated in Step C.

BRIEF DESCRIPTION OF THE DRAWINGS

The foregoing and other objects of this invention, the various features thereof, as well as the invention itself may be more fully understood from the following description when read together with the accompanying drawings in which:

FIG. 4 is a flow diagram of the calibration step of the present invention;

FIG. 5 is a flow diagram of the offset correction step of the present invention;

DETAILED DESCRIPTION

The present invention is preferably directed to an x-ray CT scanner system which is used to scan bags and packages in airports and other secure locations where the detection of contraband is essential. This invention is related to the systems disclosed in commonly-assigned U.S. Pat. Nos. 5,949,842 and 5,970,113, which are hereby incorporated herein by reference. It will be understood, however, that the present invention may also be utilized to reduce scatter in CT scanners used in the medical field and in any scanning system in which the reduction of scatter is critical to the proper reconstruction of the scanned objects.

Figure 1:
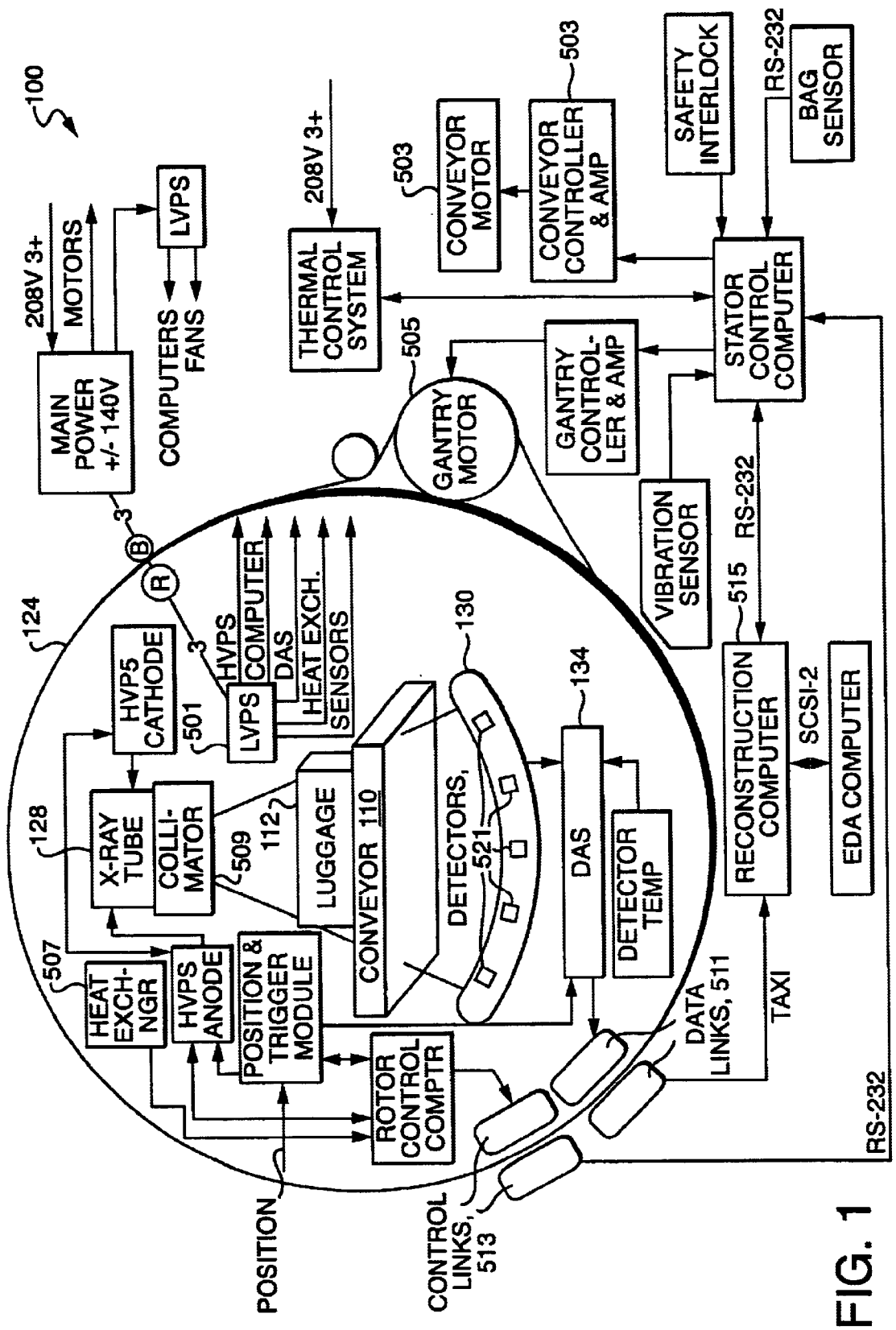
FIG. 1 is a schematic block diagram of a CT scanner in accordance with the present invention.

FIG. 1 is a mechanical/electrical block diagram of one embodiment of a baggage scanning system 100 of the invention. The mechanical gantry of the scanner 100 includes two major components, the disk 124 and the frame (not shown). The disk 124 is the rotational element which carries an X-ray assembly, a detector assembly 130, a data acquisition system (DAS) 134, a high-voltage power supply and portions of the monitor/control assembly, a power supply assembly and a data link assembly. The frame supports the entire system 100, including the baggage handling conveyor system 110. The disk 124 is mechanically connected to the frame via a duplex angular contact ball bearing cartridge. The disk 124 can be rotated at a constant rate by a belt which can be driven by a DC servomotor 505. The gantry also contains X-ray shielding on the disk and frame assemblies.

In one embodiment, the baggage conveyor system 110 includes a single belt driven at a constant rate to meet specified throughput requirements, which, in one embodiment, include a requirement that 675 bags per hour be processed. The belt can be driven by a high-torque, low-speed assembly to provide a constant speed under changing load conditions. A low-attenuation carbon graphite epoxy material can be used for the portion of the conveyor bed in the X-ray. The total length of the conveyor is designed to accommodate three average length bags. A tunnel is used around the conveyor to meet the appropriate safety requirement of a cabinet X-ray system.

In one embodiment, input power of 208 volts, 3-phase, 30 amps services as the main supply which can provide power for the entire system. This input power can be supplied by the location at which the system is installed. Power is transferred from the frame through a series of frame brushes which make continuous contact with the metal rings mounted to the disk 124. The low-voltage power supply 501 on the disk 124 provides power for the DAS 134, the X-ray cooling system and the various monitor/control computers and electronics. A low-voltage power supply on the frame provides power for the reconstruction computer and the various monitor/control electronics. The conveyor motor 503, the gantry motor 505, the high-voltage power supply and the X-ray coolant pump can all be supplied power directly from the main supply.

The high-voltage power supply provides power to the X-ray tube 128. The supply can provide a dual voltage across the cathode/anode which can be modulated at 540 Hz. The driving waveform can be in the form of a sine wave. This supply can also provide X-ray filament power. The supply current can be held approximately constant for both voltages.

The X-ray assembly includes a bipolar, fixed-anode X-ray tube 128, a heat exchanging system 507, a collimator 509, shielding, an X-ray sensor and an alignment/mounting plate. The collimator can provide an X-ray cone beam of 61° fan angle by 6° spread. The heat exchanging system 507 includes a pump, radiator, fan and plumbing. The heat transfer liquid can be a high-dielectric oil. An alignment plate can be used for mounting the tube 128 to the disk 124 to reduce the field replacement complexity and time. An X-ray sensor can be included to provide X-ray intensity feedback.

Figure 2:
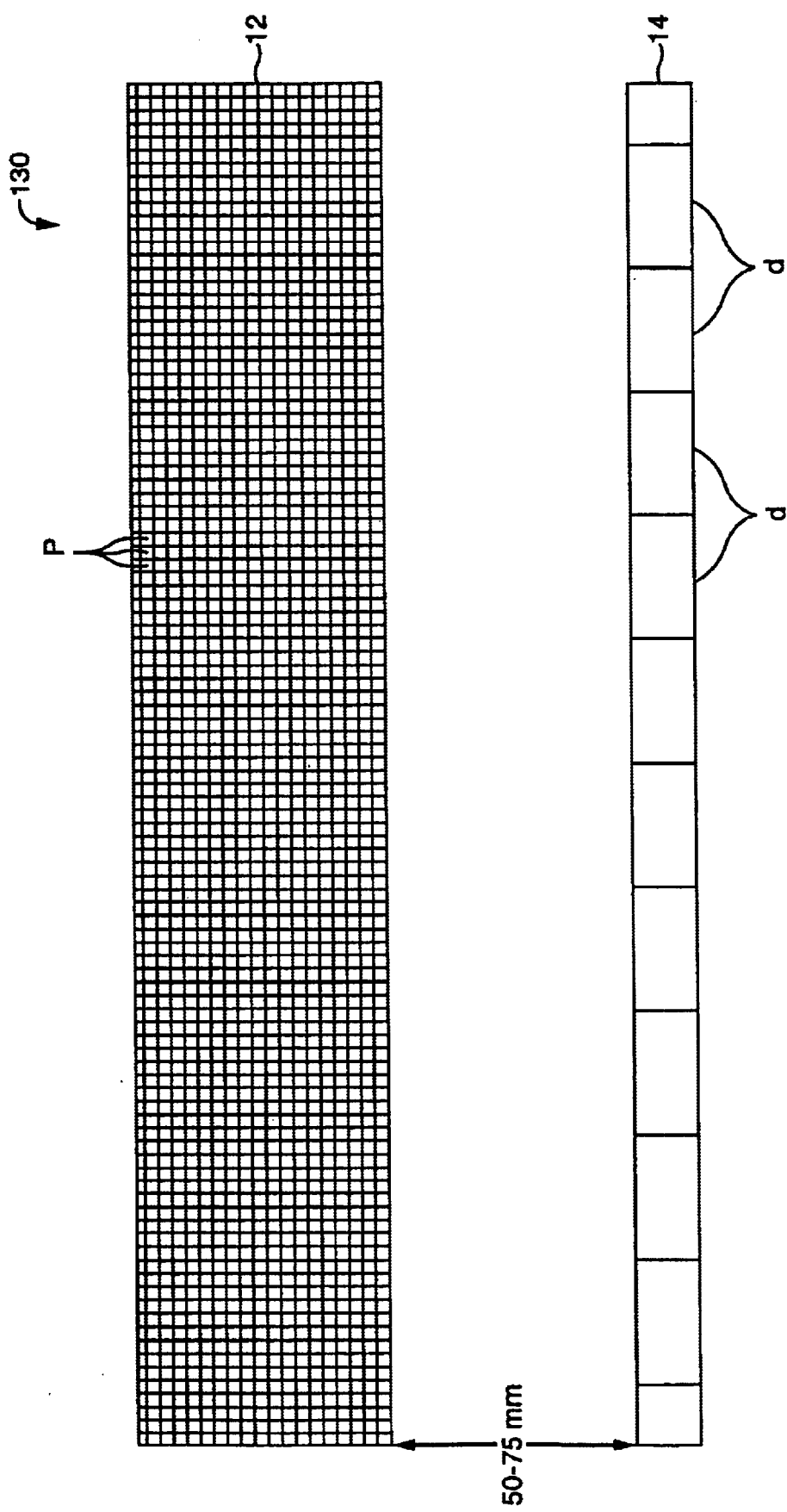
FIG. 2 is a schematic diagram of the detector array of the scanner of FIG. 1 in accordance with the present invention.

The duel-energy X-rays strike the baggage, and some portion of the X-rays pass through and strike the detector assembly 130. Detector assembly 130 is schematically shown in FIG. 2 and includes a primary array 12 of detectors and a row 14 of scatter detectors. For the purposes of this description, the detectors in the primary array 12 are generically referred to with the index "p" and detector in the scatter row 14 are generically referred to with the index "d". While not shown to scale in the figure, the array 12 can have 16 or more rows of detectors with approximately 1,000 detectors in each row. Scatter detector row 14 need only include approximately 20–40 detectors in the preferred embodiment, in order to reduce the overall cost of the system. Furthermore, any type and/or size of scatter detector may be utilized in the scatter detector row 14. Preferably, the scatter row 14 is spaced approximately 50–75 mm from the array 12. Preferably, the x-ray beam is collimated to cover a narrow path of the detectors in array 12 and the scatter detector row 14 is located outside of the penumbra of the X-ray beam to insure that the scatter detectors detect only scatter and not the main x-ray beam.

The detector assembly 130 can be made up of scintillators, photodiodes, mounting substrates and a mechanical mounting spine. A spine heater with temperature sensors 521 can also be included. The detector assembly 130 performs an analog conversion from X-ray to visible photons and then to electrical current. The scintillators are made from cadmium tungstate crystal which is thick enough to almost completely absorb all of the X-rays. The scintillators convert the X-rays into visible photons. The crystal can be surrounded on all sides except the bottom by optically reflective material. Thus, the visible photons can pass out of the bottom of the crystal. The photodiodes can be connected to the bottom of the crystal by means of an optically transmissive adhesive. The photodiodes emit a current which decreases logarithmically with the bag's X-ray attenuation. The photodiodes can be attached to a ceramic substrate which can be sized to fit several detectors.

This electrical substrate can be wire bonded and epoxied to a flexprint which contains a connector which mounts to the DAS 134. Each detector substrate can then be mechanically attached to a mounting spine that has the fan beam radius and projects in the Z-direction. This spine can then be rigidly secured to the disk 124.

The DAS 134 can sample the detector currents, multiplex the amplified voltages to a set of 16-bit analog-to-digital converters and multiplex the digital outputs to the non-contact serial data link 511. The DAS 134 can be triggered by the angular position of the disk 124.

The non-contact links 511 and 513 transfer the high-speed digital DAS data to the image reconstruction processor 515 and low-speed monitor/control signals back and forth between the disk and frame control computers. The data link 511 can be based upon an RF transmitter and receiver. The transfer protocol can be TAXI™ which is capable of up to 350 Mbits/sec. The control link 513 can be based on wireless LAN technology, which can include identical PCMCIA cards mounted in both the frame and disk computers. The cards can have both a transmitter and receiver electronics and can emulate a standard Ethernet card. A point-to-point network is therefore established for the low-speed monitor and control communication.

The image reconstructor converts the digital line integrals from the DAS 134 into a set of two-dimensional images of bag slices for both the high and low energies. The CT reconstruction can be performed via a helical-cone beam solution. The reconstructor can include embedded software, a high-speed DAS port, an array processor, a DSP-based convolver, an ASIC-based backprojector, image memory, UART control port, and a SCSI output port for image data. The array processor can perform data corrections and interpolation. The reconstructor can be self-hosted and can tag images based upon the baggage information received over the UART interface to the frame computer.

The monitor and control system can be a PC-based embedded control system. All subsystems can be monitored for key health and status information. This system can also control both motion systems, can sense baggage information, can control the environment, e.g., temperature, humidity, etc., can sense angular position of the disk 124 and can trigger the DAS and HVPS. This system can also have a video and keyboard interface for engineering diagnostics and control Additionally, a control panel can be included for field service.

Figure 3:
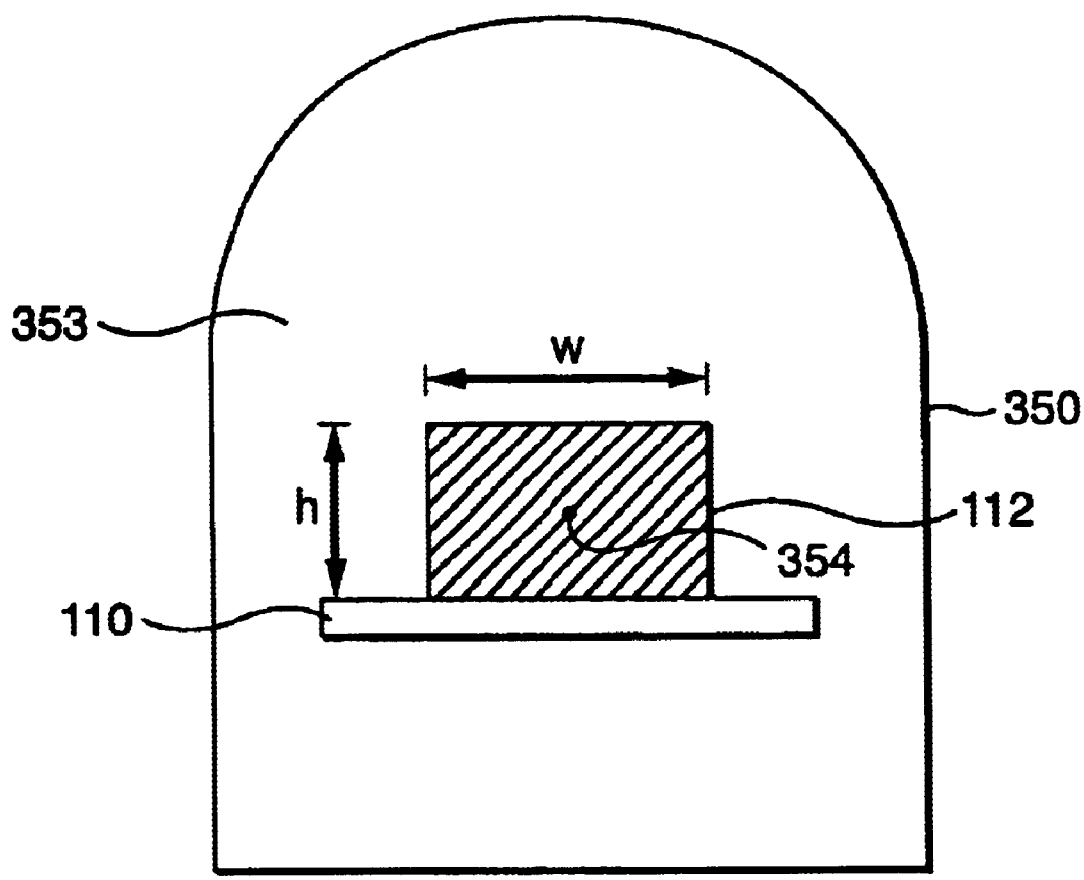
FIG. 3 is a schematic diagram of the filed-of-view of the CT scanner of FIG. 1.

FIG. 3 is a schematic pictorial diagram of the field of view of the scanner, used to illustrate the adaptive reconstruction window of the invention. The field of view is shown to include the tunnel 350 and conveyor 110 on which is located a bag 112 having a height h and a width w.

Figure 9:
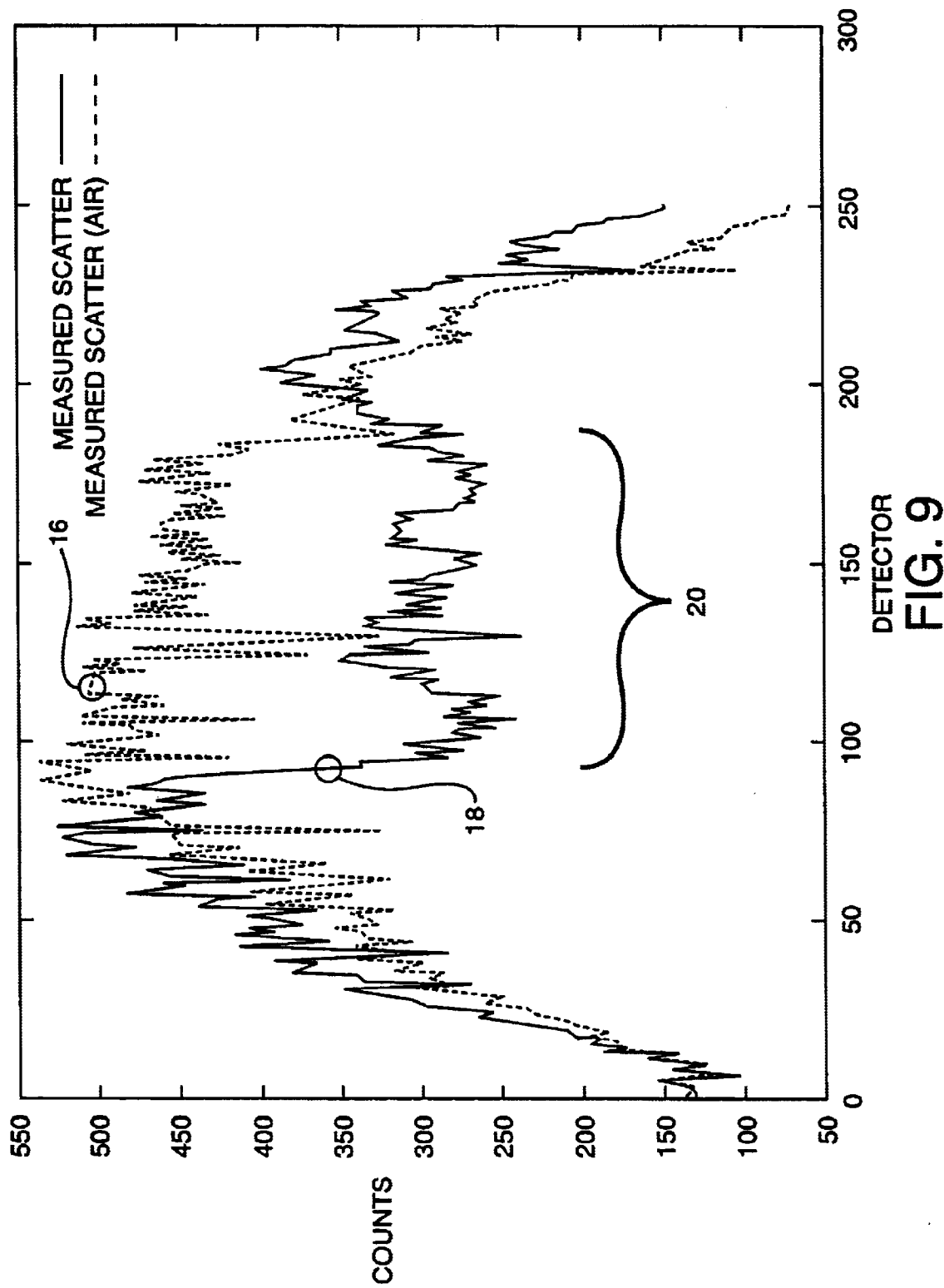
FIG. 9 is a graph showing the profile of scatter detected with and without the presence of an object within the CT scanner.

The first step according to the present invention for correcting for scatter in the scanner system is to measure the scatter within the scanner that results from the presence of the tunnel 350 and conveyor 110. This measurement is taken so that it can be compensated for when correcting for the overall scatter within the system. This step is referred to as the calibration step, because it determines the baseline amount of scatter that occurs within the scanner due to the tunnel 350 and conveyor 110. FIG. 9 shows a profile 16 of the scatter that is detected by the row 14 of scatter detectors when there is no object within the tunnel of the scanner. This measurement is referred to as the "air data" related to the scatter within the system. Shown at 18 is a profile of the scatter detected by scatter detector row 14 with an object placed on the conveyor 110 and passed through the tunnel 350. As can be seen in FIG. 9, the presence of an object within the tunnel causes the amount of scatter to drop in central region 20. This occurs as a result of the object absorbing a portion of the original scatter 16, as well as the direct x-rays.

The calibration step involves using the measured scatter in air, $S_a$, which is the scatter present in the tunnel of the scanner in the absence of a scanned object, such as that shown at 16 in FIG. 9. The view-dependent scatter, $S_a$, is estimated using several rotations of the scanner so that multiple measurements at each of a number of locations can be averaged. The scatter estimate $S_a$ due to the tunnel 350 and conveyor 110 is computed as follows:

$$S_a(v,d) = \frac{1}{N_{rot}} \sum_{r=0}^{N_{rot}-1} (S_a(r,v,d) - O(d)) \qquad (1)$$

where $N_{rot}$ is the number of rotations made by the scanner; d is the scatter detector index, $d \in \{0, \ldots, Ns_d-1\}$; v is the view index; and $Ns_d$ is the total number of scatter detectors. $S_a(r, v, d)$ is the measured scatter of the $d_{th}$ scatter detector, $v_{th}$ view, of the $r_{th}$ rotation. O(d) is the offset of the $d_{th}$ detector.

This process is shown schematically in FIG. 4. In step 22, the air data for the tunnel 350 and conveyor 110 is measured by each view of each detector for each rotation. In step 23, the offset of the detector is corrected and, in step 24, the measurements obtained are averaged over all of the scanner rotations. The result of this computation is $S_a$.

The next steps involve estimating the scatter that results from the presence of the scanned object within the scanner.

In the presence of scanned luggage, the scatter is estimated using the following steps:

The scatter data is measured, offset corrected as follows:

$$S_o(r,v,d) = (S_m(r,v,d) - O(d)) \qquad (2)$$

where r is the rotation index; v is the view index; and d is the detector index. O(d) is the offset value of the $d_{th}$ detector, $S_m$ is the measured scatter. These steps are shown in FIG. 5, wherein, in step 26, the scatter detectors d, FIG. 2, measure the scatter data, $S_m$, associated with the object being scanned and, in step 27, the scatter data $S_m$ is offset corrected, resulting in the offset-corrected scatter $S_o$.

Figure 6:
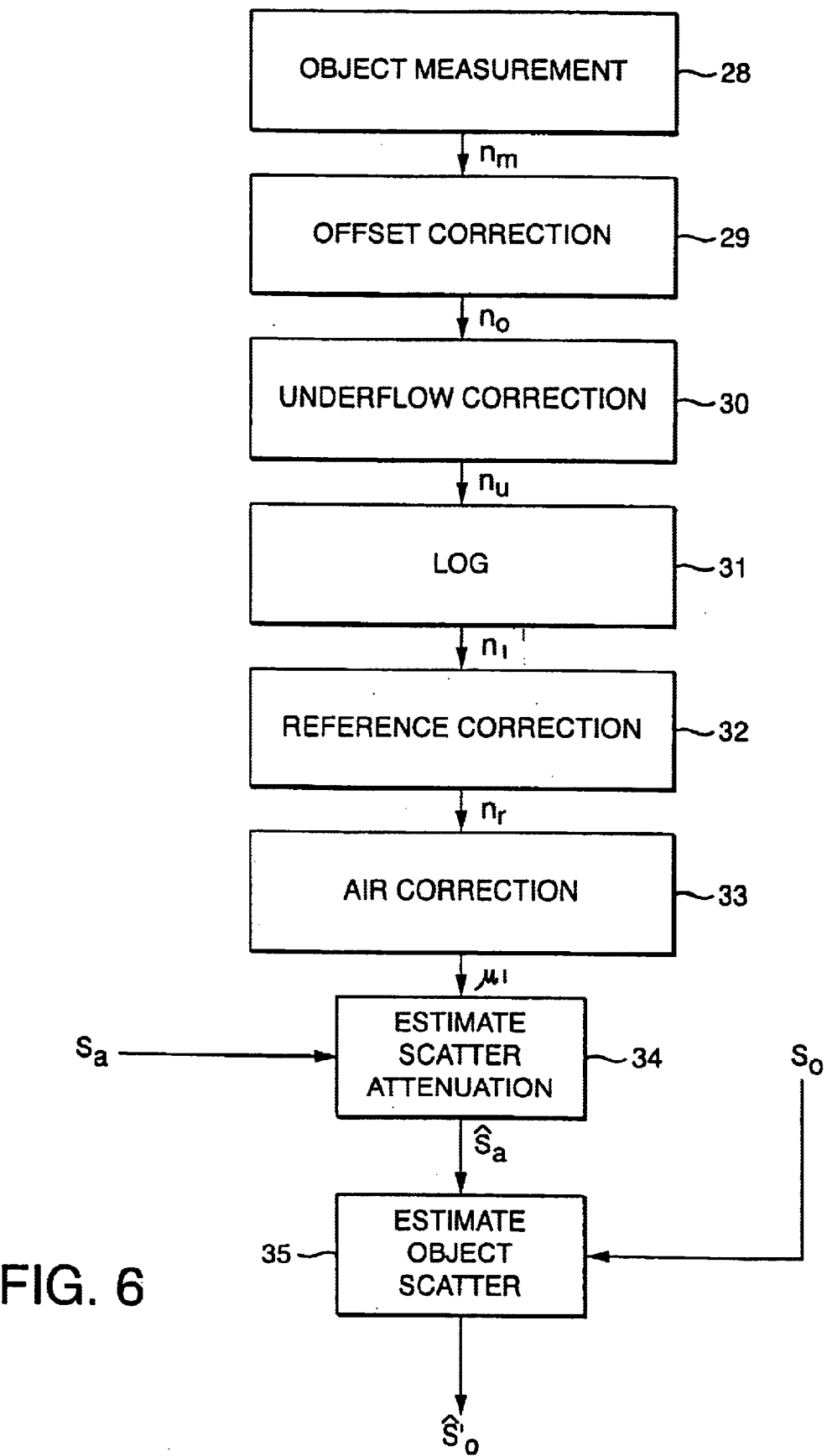
FIG. 6 is a flow diagram of the scatter estimate step of the present invention.

Next, the attenuation, $\mu l(r,v,d)$, caused by the object being scanned is calculated using the measured projection, $n_m$ (r,v,d) of the object, which is the signal $n_m$ detected by the primary detectors p, step 28, FIG. 6. The measured projection $n_m$ is then offset corrected, step 29, according to the equation:

$$n_o(r,v,p) = n_m(r,v,p) - O(p) \qquad (3)$$

where $n_m$ is the measured counts; $n_o$ is the offset corrected data; and p is the primary detector index.

In step 30, the offset-corrected data $n_o$ is corrected for under-flow, to insure that no detector has an offset less than 1. The under-corrected data $n_u$ is calculated according to the following equation:

$$n_u(r,v,p) = \begin{cases} n_o(r,v,p) & \text{if } n_o(r,v,p) > 1 \\ 1 & \text{Otherwise} \end{cases} \qquad (4)$$

In step 31, the logarithmic value $n_l$ of the under-corrected data $n_u$ is calculated and the offset corrected reference $r_l$ is determined as follows:

$$n_l(r,v,p) = \log\{n_u(r,v,p)\} r_l(r,v) = \log\{r_m(r,v) - O(\text{ref})\} \qquad (5)$$

where $r_m$ is the measured reference value; and O(ref) is the reference detector offset.

In step 32, a reference correction operation is carried out to obtain the reference-corrected measurement $n_r$:

$$n_r(r,v,p) = n_l(r,v,p) - r_l(r,v) \qquad (6)$$

The reference-corrected measurement $n_r$ is air corrected, or subtracted from the signal a(v,p) received in the primary array without the presence of an object in the scanner, step 33, to obtain the attenuation, $\mu l(r,v,d)$, caused by the object being scanned:

$$g(r,v,p)=a(v,p)-n_r(r,v,p) \quad (7)$$

The attenuation of the tunnel 350 and the conveyor 110 scatter through the object is then calculated in step 34, using the computed attenuation:

$$\hat{S}_a(r,v,d)=\lambda S_a(v,d)e^{-\mu l(r,v,d)}+(1-\lambda)S_a(v,d) \quad (8)$$

where $0 \leq \lambda \leq 1$; $\lambda$ represents the fraction of the tunnel and the conveyor scatter that goes through the scanned object. The term $\mu l(r,v,d)$ is the equivalent attenuation detected by each scatter detector:

$$\mu l(r, v, d) = \frac{N_{sd}}{N_d} \sum_{p=0}^{N/N} \mu l\left(r, v, p + \frac{dN_d}{N_{sd}}\right) \quad (9)$$

Based on the foregoing, the scatter through the object only is estimated in step 35 according to the equation:

$$\hat{S}'_o(r,v,d)=\hat{S}_o(r,v,d)-\hat{S}_a(r,v,d) \quad (10)$$

Once the scatter through the object only, $\hat{S}'_o$, is determined, any discrepancies in the detected scatter due to inaccurate, missing or malfunctioning scatter detectors must be accounted for. This is done as follows:

First, replace the value of missing or malfunctioning scatter detectors d using linear interpolation:

$$\hat{S}_o(r, v, d) = \begin{cases} G\hat{S}_o(r, v, d) & \text{if } d \text{ is not missing} \\ 0.5(\hat{S}'_o(r, v, d-1) + \hat{S}'_o(r, v, d+1)) & \text{if } d \text{ is missing or malfunctioning} \end{cases} \quad (11)$$

At the boundary, malfunctioning detectors are replaced by their nearest neighbors.

Next, perform gain calibration and underflow correction here to obtain the corrected object scatter $\hat{S}_o$:

$$\hat{S}_o(r, v, d) = \begin{cases} G\hat{S}_o(r, v, d) & \text{if } \hat{S}_o(r, v, d) > 1 \\ G & \text{Otherwise} \end{cases} \quad (12)$$

where G is a normalization factor that depends on the efficiencies and surfaces of the scatter and primary detectors:

$$G = \frac{\text{Surface of primary detector}}{\text{Surface of scatter detector}} \quad (13)$$

Figure 7:
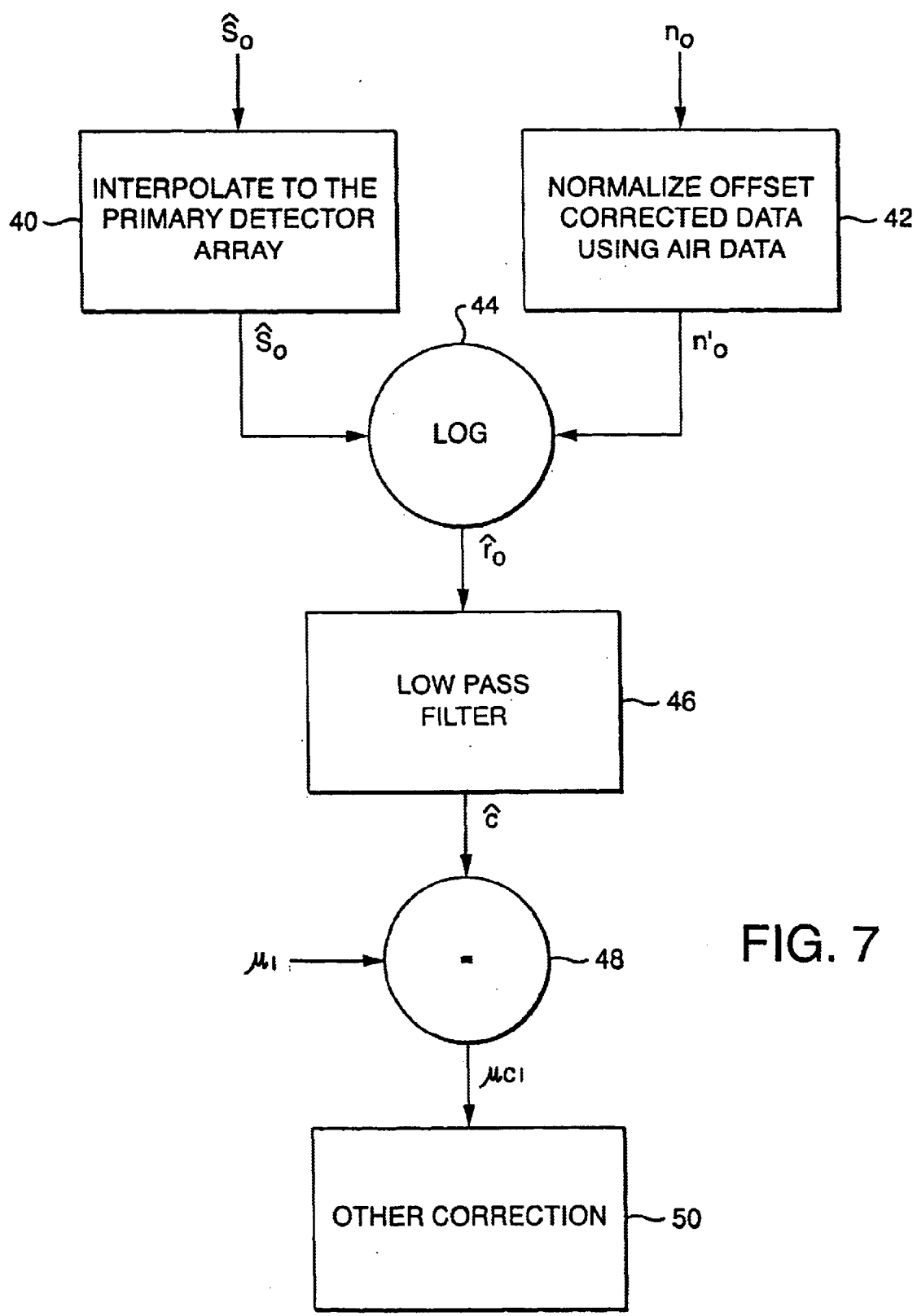
FIG. 7 is a flow diagram of the scatter correction step of the present invention.

Once the corrected object scatter $\hat{S}_o$ is determined, the he scatter correction is accomplished in the log domain as follows:

First, the scatter of the primary detector is computed, preferably using an $N_l$-point Lagrange interpolation:

$$\hat{S}_o(r, v, p) = \sum_{l=0}^{N-1} L_c(l)\hat{S}_o(r, v, I(p)+l-N/2+1) \quad (14)$$

where p is the index of primary detector, $s \in \{0, \ldots, N_d-1\}$; $N_d$ is the number of primary detectors; $L_c$, are the Lagrange coefficients; and I(p) is the index of the nearest scatter detector to the primary detector p. I(p) is computed as follows:

$$I(p)=[pN_{sd}/N_d] \quad (15)$$

where $N_{sd}$ is the number of scatter detectors. Detectors at the boundaries of the detector array are interpolated, step 40, FIG. 7, using the nearest neighbor interpolation:

$$\hat{S}_o(r,v,p)=\hat{S}_o(r,v,0) \text{ for } p=0,\ldots, N_d/N_{sd}-1 \hat{S}_o(r,v,p)=\hat{S}_o(r,v,N_{sd}-1)$$
$$\text{for } p=N_d-N_d/N_{sd}, \ldots, N_d-1 \quad (16)$$

In step 42, the gain of the offset corrected data $n_o$ is normalized using the air data a(v, d):

$$n'_o(r, v, p) = \frac{\arg_p \max a(v, p)}{a(v, p)} n_o(r, v, p) \quad (17)$$

where $n_o(r,v,p)$ is the offset corrected data, $p \in \{0, \ldots, N_d-1\}$.

In step 44, the correction vector $\hat{r}_o$ is computed using the ratio of estimated scatter to the offset corrected projections:

$$\hat{r}_o(r, v, p) = \log\left\{1.0 - \frac{\alpha \hat{S}_o(r, v, p)}{n'_o(r, v, p)}\right\} \quad (18)$$

where $\alpha$ is a scale factor used to tune and calibrate the scatter correction. Due to the limited dynamic range of the logarithm arguments, [0, 1], a 1000-point lookup table can be used to compute the correction vector.

In step 46, the correction vector $\hat{r}_o$ is low-pass filtered, using a (2M+1)-point Boxcar filter:

$$\hat{c}(r, v, p) = \frac{1}{2M+1} \sum_{i=-M}^{M} (\hat{r}_o(r, v, p+i)) \quad (19)$$

for $p \in M, \ldots, N-M-1$, and:

$$\hat{c}(r,v,p)=\hat{r}_o(r,v,p) \text{ for } i=0,\ldots, M-1 \text{ and } i=N-M, \ldots, N-1 \quad (20)$$

Finally, in step 48, the air-corrected data of the scanned object $\mu_c l$ is calculated:

$$\mu_c l(r,v,p)=\mu l(r,v,p)-\hat{c}(r,v,p) \quad (21)$$

Other corrections, such as water calibration and data base deringing can now be applied to the scatter corrected data in step 50.

As set forth above, once the scatter through the object only, $\hat{S}'^o$, is determined, any discrepancies in the detected scatter due to inaccurate, missing or malfunctioning scatter detectors must be accounted for. The following section describes the process for detecting malfunctioning scatter detectors.

Generally, scatter detectors are considered to be malfunctioning if they fail an offset specification criterion. However, it has been found that, on certain scanners, scatter detectors are able satisfy their offset specification and yet have bad readings. As a result of this, a malfunctioning scatter detection procedure has been implemented that will help identify such detectors.

The procedure uses the offset corrected scatter tables generated by the scatter calibration process, and a set of a second-order polynomial coefficients that model the ideal scatter profile of the scanner. The procedure is as follows:

First, calculate the average scatter calibration data for every scatter detector d according to the equation:

$$S_{avg}(i, sd) = \frac{1}{Ns} \sum_{v=0}^{v=Ns-1} S(v, sd) \tag{22}$$

where v is the index of the scatter segment, $v \in \{0, \ldots, Ns-1\}$; Ns is the number of scatter segments; sd is the index of the scatter detector, $sd \in \{0, \ldots, N_{sd}-1\}$; and where $N_{sd}$ is the number of scatter detectors.

Next, for all $sd \in \{0, \ldots, N_{sd}-1\}$ apply the following:

$$I(sd) = \begin{cases} 0 & \text{if } S_{min} < S_{avg}(sd) < S_{max} \\ 1 & \text{Otherwise} \end{cases} \tag{23}$$

Figure 8:
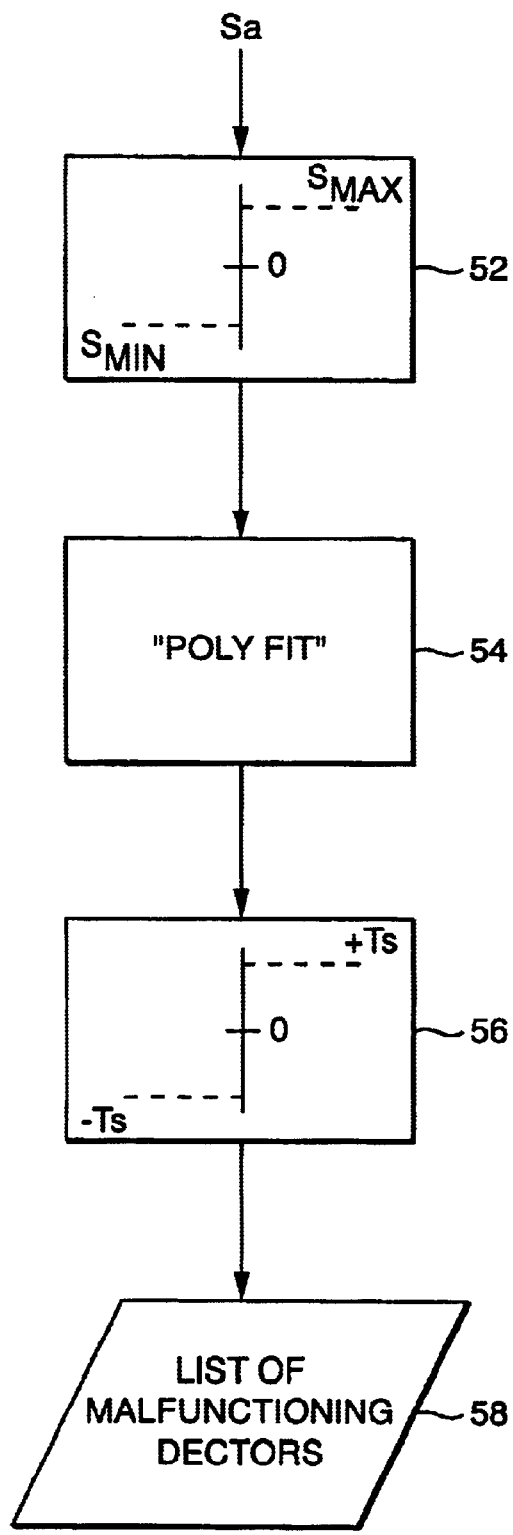
FIG. 8 is a flow diagram of the malfunctioning detector identification step of the present invention.

I(sd) is the bad detector indicator, a 0 indicates a good scatter detector and 1 indicates a bad detector. $S_{max}$ and $S_{min}$ are the boundaries of the scatter counts. This step is shown schematically at step 52 of FIG. 8.

In step 54, compute the second order polynomial using the set of coefficients:

$$p(sd) = C_2 x(sd)^2 + C_1 x(sd) + C_0 \tag{24}$$

$C_j$ for j=0, 1, 2, are the polynomial coefficients, $x(sd) = sd - 0.5(N_{sd}-1)$.

Then, in step 56, the malfunctioning scatter detectors are defined as follows:

$$I(sd) = \begin{cases} 1 & \text{if } |S_{avg}(sd) - p(sd)| > T_s \\ 0 & \text{Otherwise} \end{cases} \tag{25}$$

where $T_s$ is a predetermined threshold for determining whether, in step 56, the detectors satisfy the operating requirements. Based on this calculation, a list of malfunctioning detectors 58 is generated.

Figure 10:
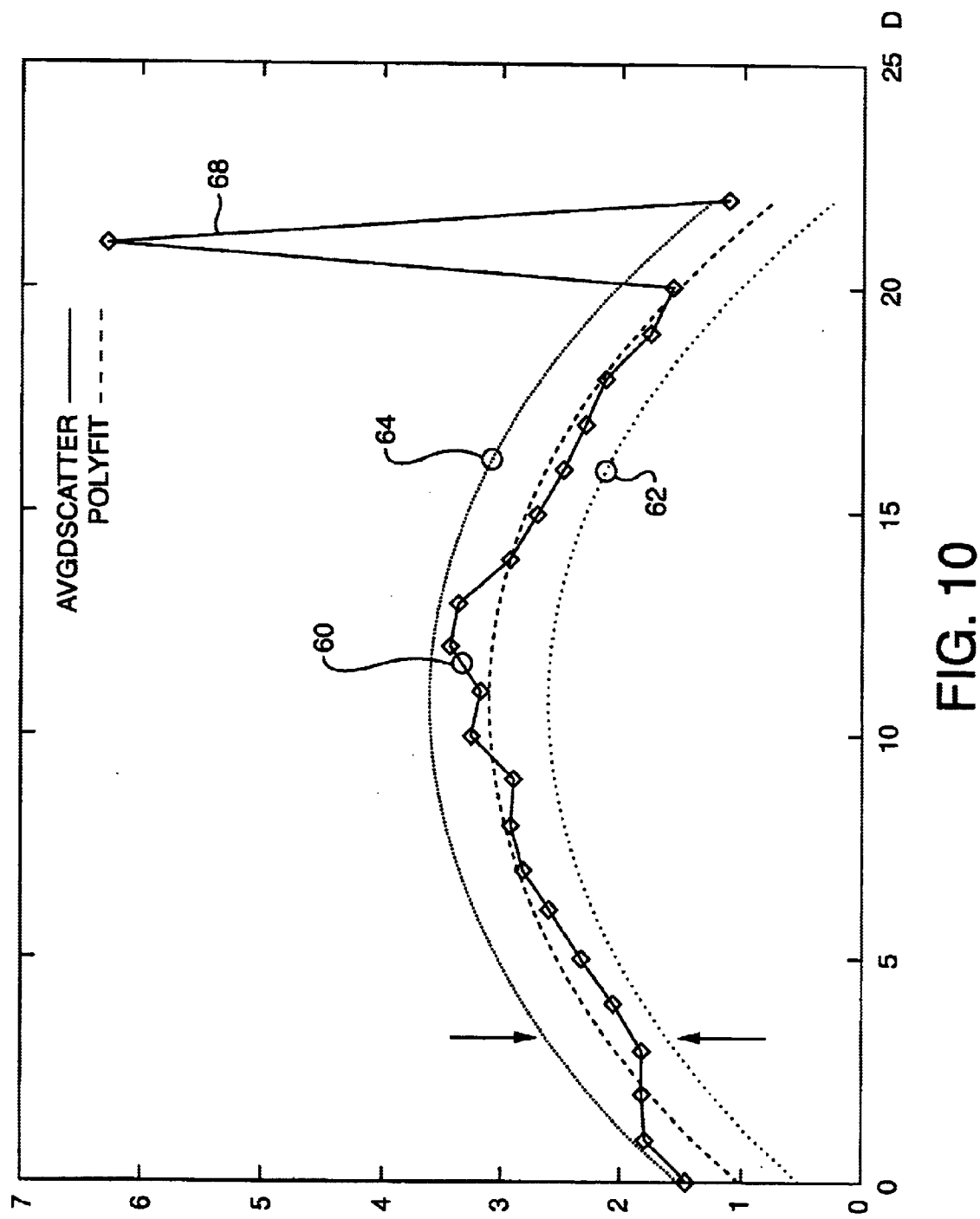
FIG. 10 is a graph showing the calibration measurements of scatter detectors, including a malfunctioning detector.

FIG. 10 is a graph of the result of the process described above and shown in FIG. 8. As shown in the figure, the interpolated reading of each scatter detector d is shown at 60. The minimum detector threshold $S_{min}$ is shown at 62, the maximum detector threshold $S_{max}$ is shown at 64 and the average $S_{avg}$ is shown at 60. According to FIG. 10, all of the scatter detectors d have a calibration value S which falls between the minimum and maximum threshold values 62, 64, except for the detector having the reading shown at 68. This detector will be placed on the list of malfunctioning detectors 58, and the measured values for each of the detectors adjacent to the malfunctioning detector will be averaged in order to obtain a value that falls within the minimum and maximum threshold.

The polynomial coefficients referenced above are generated by averaging several sets of air data a. The coefficients for a given set are generated as follows:

1. Average the scatter calibration data for every scatter detector:

$$S_{avg}(sd) = \frac{1}{Ns} \sum_{v=0}^{v=Ns-1} S(v, sd) \tag{26}$$

2. Compute the second-order difference of the averaged scatter values:

$$a(sd) = |S_{avg}(sd) - 0.5(S_{avg}(sd-1) + S_{avg}(sd+1))| \tag{27}$$

3. Compute the Z-score threshold of the second order differences:

$$z(sd) = \frac{a(sd) - \bar{a}(i)}{\sigma_a(i)} \tag{28}$$

where $\bar{a}(i)$ and $\sigma_a(i)$ are the mean and the standard deviation of the second-order difference.

4. Find the best polynomial fits of the averaged scatter points whose z scores are less than a certain threshold value, $T_z$, and satisfy the following condition, $S_{min} < S_{avg}(sd) < S_{max}$. $S_{max}$ and $S_{min}$ are the boundaries of the scatter counts.

The scatter correction uses the offset corrected data of the scanned object for estimating the error introduced by scatter. The offset corrected data is not normalized for detector gain, as a result, any variation in detector gain would be reflected in the reconstructed images. Variation of the detector gain will have to be normalized in order to generate artifact free images.

The data from the air table will be used in the normalization process. The offset corrected data is normalized as follows:

$$P_o^n(v, s) = \frac{\max_s (a(v, s))}{a(v, s)} P_o(v, s) \tag{29}$$

where, $s \in \{0, \ldots, N_s-1\}$ is the detector index, $N_s$, is the number of detectors; $v \in \{0, \ldots, N_v-1\}$ is the view index; $N_v$ the number of views; $P_o(v, s)$ is the offset corrected projection data; a(v, s) is its corresponding air table element; and $P_o^n(v, s)$ is the normalized offset corrected projection.

Accordingly, the present invention provides a method of and system for scatter correcting in a computed tomography scanner which includes, in addition to a primary array of detectors, a row of scatter detectors oriented with respect to the array such that the row of scatter detectors is only able to detect scattered radiation and not radiation which is directly received by the primary array of detectors. A calibration measurement is first taken, which measures the scatter associated with the scanner tunnel and conveyor before in the absence of an object to be scanned. Once this scatter profile is determined, the amount of scatter associated with an object within the scanner can be estimated by effectively subtracting the scanner-associated scatter from the scatter detected when the object is within the scanner. The invention eliminates the need for expensive and complex anti-scatter plates and enables the scanner to provide reconstructed images having reduced artifacts due to scattering.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A system for correcting for scatter in a computed tomography scanner comprising:

a tunnel having a platform disposed therein for receiving an object to be scanned;

an x-ray source for directing x-rays at the object to be scanned;

a detector array including a plurality of primary detectors for receiving said x-rays and at least one secondary detector for receiving portions of said x-ray beam scattered within said tunnel; and processing means for reducing the effects of scatter in images of the object reconstructed from the x-rays detected by said primary detectors, said processing means performing the steps of:

A. determining an amount of scatter detected by said at least one secondary detector resulting from said tunnel and said platform prior to the placement of the object on said platform;

B. determining an amount of scatter detected by said at least one secondary detector resulting from said tunnel, said platform and the object after the object has been placed on said platform;

C. estimating an amount of scatter caused only by the presence of the object on said platform within said tunnel; and D. correcting the reconstructed images of the object based on the amount of scatter estimated in Step C.

2. A method of correcting for scatter in a computed tomography scanner having platform for receiving an object to be scanned, the platform being disposed within a tunnel, a primary detector array for detecting x-rays provided by and x-ray source and a secondary detector array for detecting scattered x-rays from said x-ray source, the method comprising:

A. determining an amount of scatter detected by said secondary detector array resulting from the tunnel and the platform prior to the placement of the object on the platform;

B. determining an amount of scatter detected by said secondary detector array resulting from the tunnel, the platform and the object after the object has been placed on the platform;

C. estimating an amount of scatter caused only by the presence of the object on the platform within the tunnel; and D. correcting reconstructed images of the object based on the amount of scatter estimated in Step C.

* * * * *